US008926476B2

(12) United States Patent
Abuelsaad et al.

(10) Patent No.: US 8,926,476 B2
(45) Date of Patent: *Jan. 6, 2015

(54) ROUTINE-BASED MANAGEMENT OF EXERCISE EQUIPMENT ACCESS

(71) Applicant: International Business Machines Corporation, Armonk, NY (US)

(72) Inventors: Tamer E. Abuelsaad, Poughkeepsie, NY (US); John E. Moore, Jr., Brownsburg, IN (US); Rajeshkumar N. Singi, Marietta, GA (US); Robert R. Wentworth, Round Rock, TX (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/299,134

(22) Filed: Jun. 9, 2014

(65) Prior Publication Data

US 2014/0288960 A1    Sep. 25, 2014

Related U.S. Application Data

(63) Continuation of application No. 13/196,416, filed on Aug. 2, 2011, now Pat. No. 8,821,351.

(51) Int. Cl.
*A63B 24/00* (2006.01)
(52) U.S. Cl.
USPC ........................................ 482/8; 482/1; 482/9
(58) Field of Classification Search
USPC ............................ 482/1, 9, 900–902; 434/247
See application file for complete search history.

(56) References Cited

U.S. PATENT DOCUMENTS

| 5,435,799 | A | * | 7/1995 | Lundin | 482/8 |
|---|---|---|---|---|---|
| 6,332,094 | B1 | * | 12/2001 | Gorman | 600/520 |
| 6,576,272 | B1 | * | 6/2003 | Blechman | 424/736 |
| 6,949,052 | B2 | | 9/2005 | Millington et al. | |
| 7,670,264 | B2 | * | 3/2010 | Davis | 482/8 |
| 7,722,503 | B1 | * | 5/2010 | Smith et al. | 482/8 |
| 8,454,437 | B2 | * | 6/2013 | Dugan et al. | 463/31 |
| 8,727,948 | B2 | * | 5/2014 | Herranen | 482/8 |
| 2003/0100406 | A1 | | 5/2003 | Millington et al. | |
| 2005/0010426 | A1 | | 1/2005 | Chen et al. | |
| 2006/0058156 | A1 | | 3/2006 | Cohen et al. | |
| 2006/0180647 | A1 | | 8/2006 | Hansen | |
| 2006/0223674 | A1 | | 10/2006 | Korkie | |

(Continued)

OTHER PUBLICATIONS iFit, http://www.ifit.com/iFitLive/contentAboutiFit.do, 1 page, printed Aug. 2, 2011.

(Continued)

*Primary Examiner* — Glenn Richman
(74) *Attorney, Agent, or Firm* — Matthew Chung; Hoffman Warnick LLC

(57) ABSTRACT

A solution for managing access to exercise equipment in a fitness facility is provided. A planned exercise routine for a user, which includes data corresponding to a plurality of exercises desired to be performed by the user at the fitness facility is used for providing location information for presentation to the user. Each exercise can require use of an exercise apparatus. The exercise can be mapped to at least one exercise apparatus located at the fitness facility. A target exercise apparatus can be identified from the mapped exercise apparatus (es). Location information for one or more of the target exercise apparatuses can be provided for presentation to the user.

20 Claims, 4 Drawing Sheets

(56) References Cited

U.S. PATENT DOCUMENTS

| | | |
|---|---|---|
| 2007/0219059 A1 | 9/2007 | Schwartz et al. |
| 2007/0265138 A1 | 11/2007 | Ashby |
| 2008/0300914 A1 | 12/2008 | Karkanias et al. |
| 2010/0095209 A1 | 4/2010 | Gupta et al. |
| 2010/0331147 A1 | 12/2010 | Mikan et al. |
| 2011/0090092 A1 | 4/2011 | Birrell et al. |
| 2011/0179068 A1 | 7/2011 | O'Brien |
| 2013/0066449 A1* | 3/2013 | Verstegen et al. .............. 700/91 |

OTHER PUBLICATIONS

Richman, Notice of Allowance and Fee(s) Due for U.S. Appl. No. 13/196,416 dated Apr. 29, 2014, 12 pages.

* cited by examiner

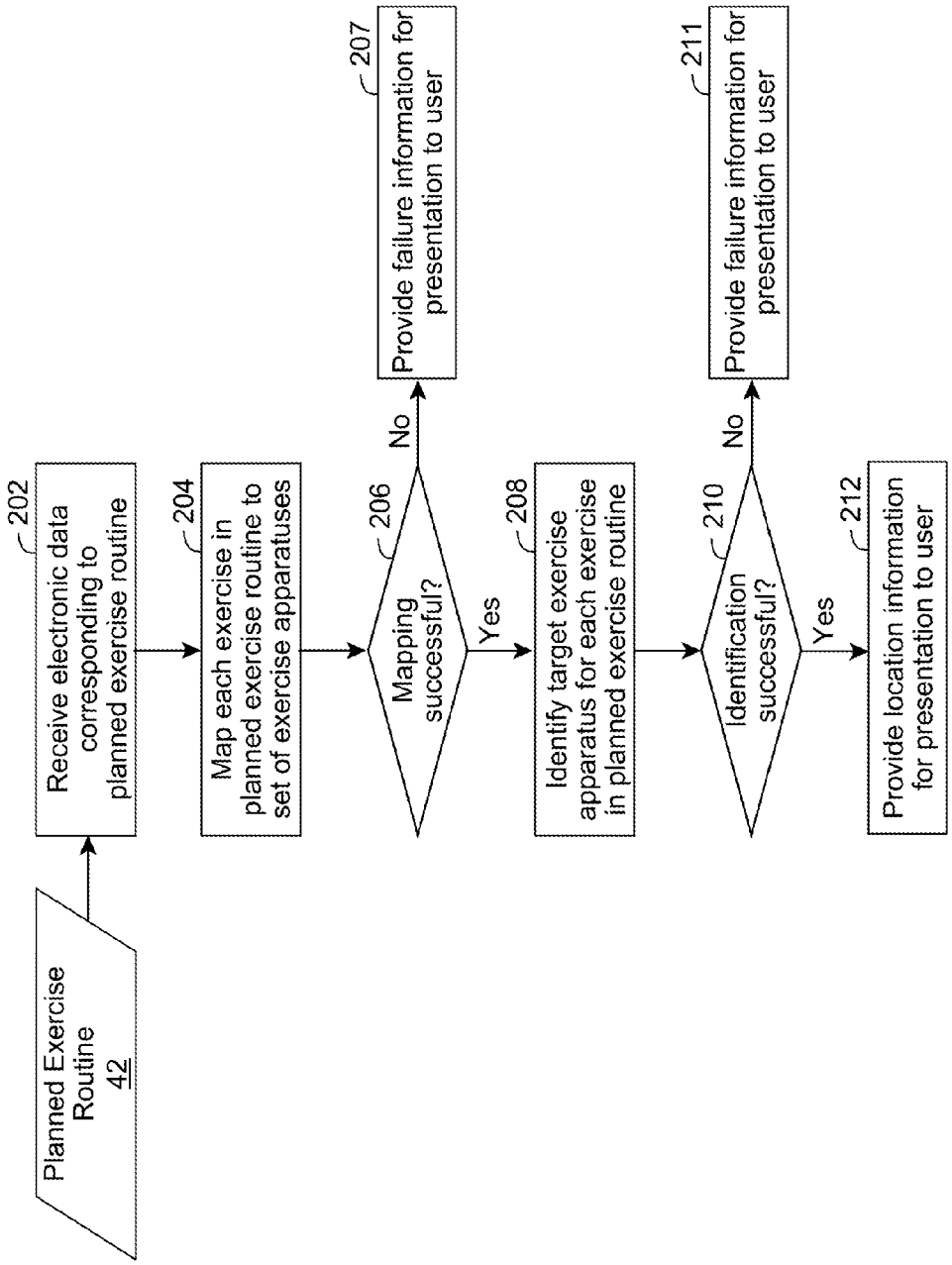

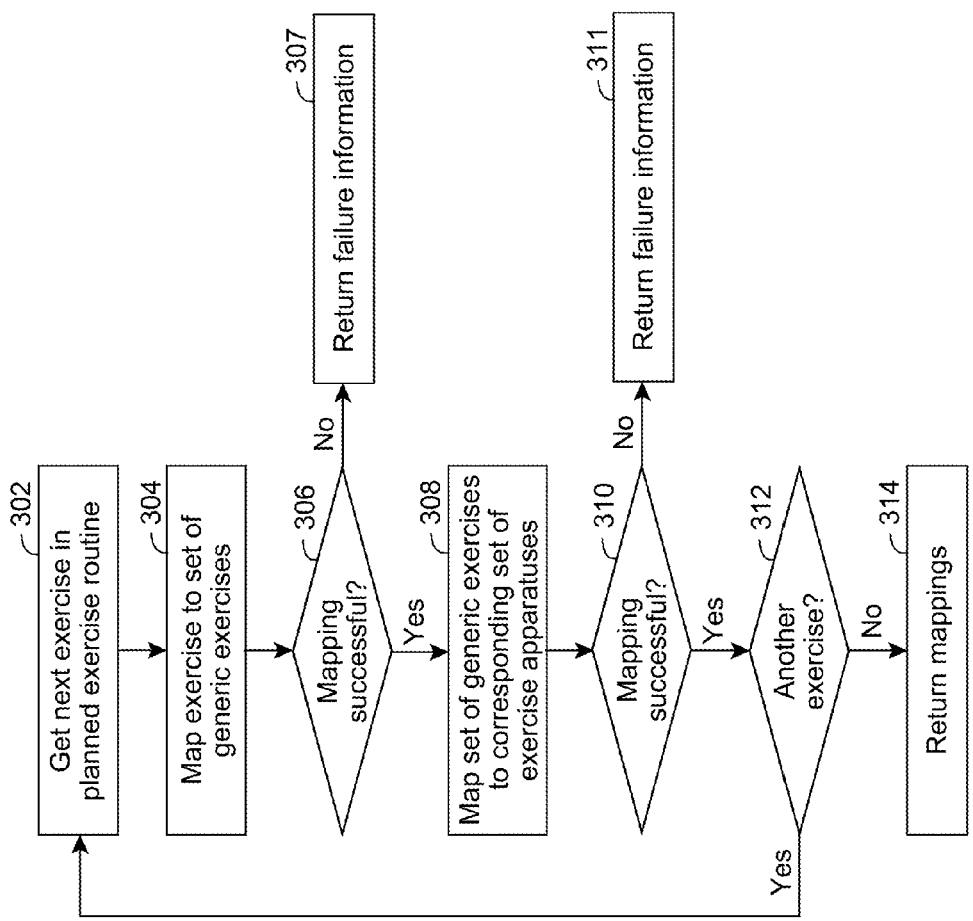

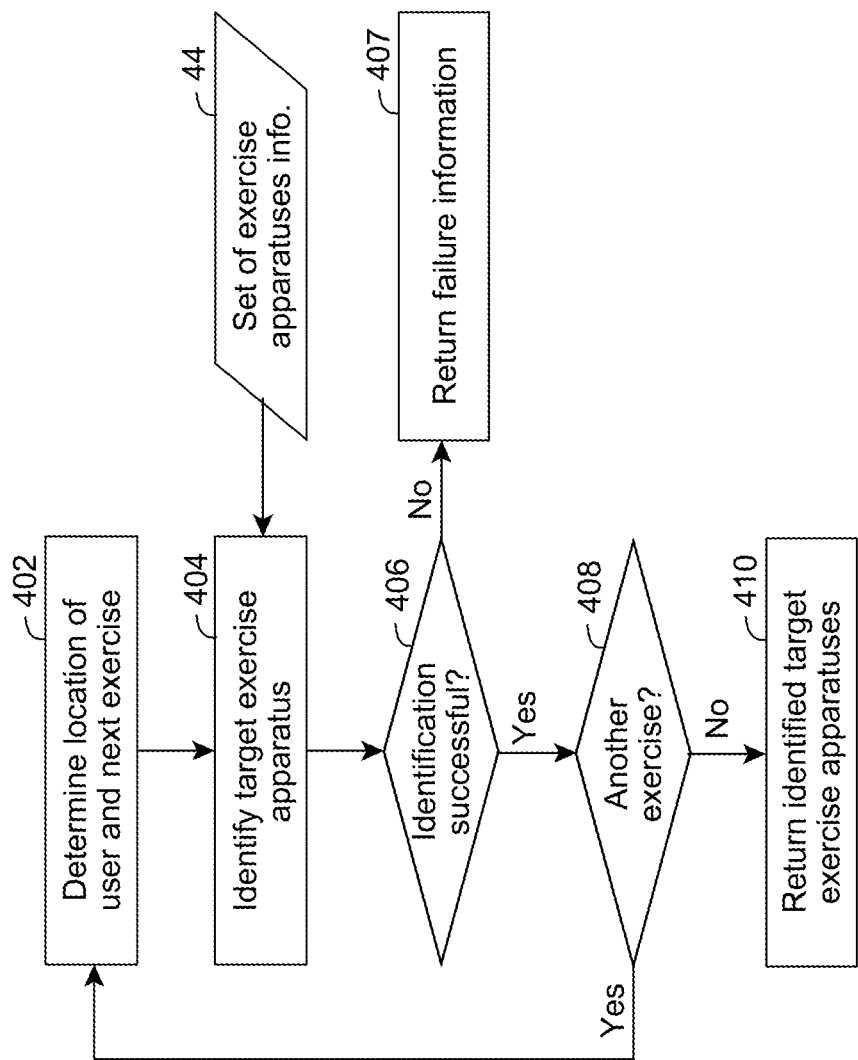

ROUTINE-BASED MANAGEMENT OF EXERCISE EQUIPMENT ACCESS

TECHNICAL FIELD

The disclosure relates generally to managing access to exercise equipment in a fitness facility, and more particularly, to managing such access using a planned exercise routine for an individual.

BACKGROUND ART

Often, when an individual goes to a fitness facility (e.g., gym), all the apparatuses (e.g., tools and accessories) required for his/her desired workout may not be in an anticipated location, or even in a single location. For example, a cable pull biceps curl bar or half increment weights may be attached to another machine or located in another part of the fitness facility. The individual can spend a lot of valuable time trying to locate all the apparatuses required to perform the workout. This can result in frustration on the part of the individual, and possibly abandonment of his/her workout routine. Even more, sufficient dissatisfaction can result in the individual dropping his/her membership with the fitness facility.

Various approaches have been proposed to assist individuals in performing their workouts in a fitness facility. One approach provides assistance with tracking an operating status of fitness equipment within the fitness facility and alerting individuals in the event of an outage. Similarly, other approaches provide an ability for an individual to reserve equipment for his/her use. Furthermore, another approach provides a 'circuit' path of exercises, which helps ensure a proper work out while reducing down time.

SUMMARY OF THE INVENTION

To date, no solution has been provided which seeks to provide all individuals concurrently using the fitness facility with flexibility, while also reducing the amount of time required for an individual to locate suitable exercise apparatus(es) for his/her planned exercise routine. Embodiments of the invention can provide such a solution.

Aspects of the invention provide a solution for managing access to exercise equipment in a fitness facility. A planned exercise routine for a user, which includes data corresponding to a plurality of exercises desired to be performed by the user at the fitness facility is used for providing location information for presentation to the user. Each exercise can require use of an exercise apparatus. The exercise can be mapped to at least one exercise apparatus located at the fitness facility. A target exercise apparatus can be identified from the mapped exercise apparatus(es). Location information for one or more of the target exercise apparatuses can be provided for presentation to the user.

A first aspect of the invention provides a computer-implemented method of managing access to exercise equipment in a fitness facility, the method comprising: obtaining, via a computer system, electronic data corresponding to an exercise routine for a user, wherein the planned exercise routine includes an exercise desired to be performed by the user at the fitness facility; mapping the exercise to at least one exercise apparatus located at the fitness facility using the computer system; identifying a target exercise apparatus at the fitness facility for the exercise from the at least one exercise apparatus located at the fitness facility using the computer system; and providing location information for the target exercise apparatus corresponding to the exercise in the planned exercise routine for presentation to the user.

A second aspect of the invention provides a computer system for managing access to exercise equipment in a fitness facility by performing a method, the method comprising: obtaining electronic data corresponding to an exercise routine for a user, wherein the planned exercise routine includes an exercise desired to be performed by the user at the fitness facility; mapping the exercise to at least one exercise apparatus located at the fitness facility; identifying a target exercise apparatus at the fitness facility for the exercise from the at least one exercise apparatus located at the fitness facility; and providing location information for the target exercise apparatus corresponding to the exercise in the planned exercise routine for presentation to the user.

A third aspect of the invention provides a computer program comprising program code embodied in at least one computer-readable storage medium, which when executed, enables a computer system to implement a method of managing access to exercise equipment in a fitness facility, the method comprising: obtaining electronic data corresponding to an exercise routine for a user, wherein the planned exercise routine includes an exercise desired to be performed by the user at the fitness facility; mapping the exercise to at least one exercise apparatus located at the fitness facility; identifying a target exercise apparatus at the fitness facility for the exercise from the at least one exercise apparatus located at the fitness facility; and providing location information for the target exercise apparatus corresponding to the exercise in the planned exercise routine for presentation to the user.

A fourth aspect of the invention provides a method of generating a computer system, the method comprising: providing a computer system for managing access to exercise equipment in a fitness facility, wherein the managing includes: obtaining electronic data corresponding to an exercise routine for a user, wherein the planned exercise routine includes an exercise desired to be performed by the user at the fitness facility; mapping the exercise to at least one exercise apparatus located at the fitness facility; identifying a target exercise apparatus at the fitness facility for the exercise from the at least one exercise apparatus located at the fitness facility; and providing location information for the target exercise apparatus corresponding to the exercise in the planned exercise routine for presentation to the user.

Other aspects of the invention provide methods, systems, program products, and methods of using and generating each, which include and/or implement some or all of the actions described herein. The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIG. 2 shows an illustrative method for providing location information for an exercise routine for presentation to a user according to an embodiment.

FIG. 3 shows an illustrative method for mapping exercises in the planned exercise routine to exercise apparatuses in a fitness facility according to an embodiment.

FIG. 4 shows an illustrative method for identifying a target exercise apparatus for an exercise according to an embodiment.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 1:
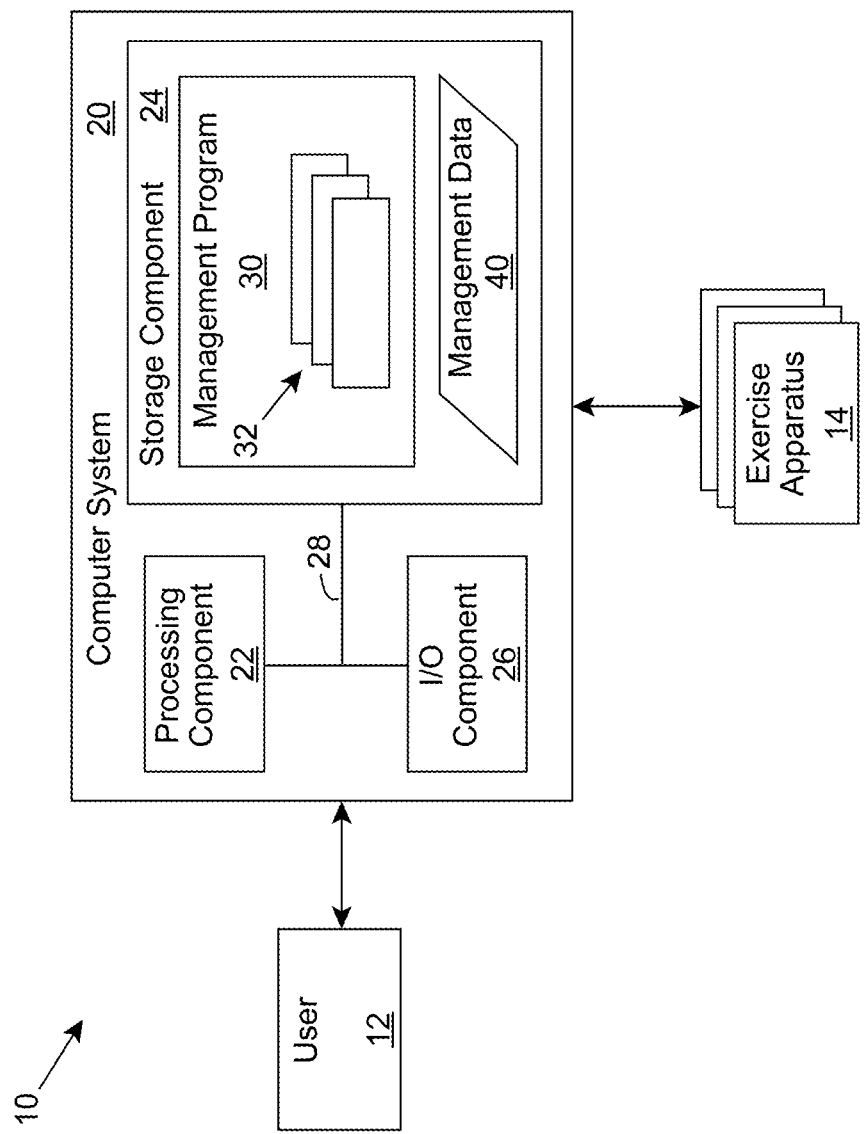
FIG. 1 shows an illustrative environment for managing access to exercise equipment in a fitness facility according to an embodiment.

As indicated above, aspects of the invention provide solutions for managing access to exercise equipment in a fitness facility. A planned exercise routine for a user, which includes data corresponding to a plurality of exercises desired to be performed by the user at the fitness facility is used for providing location information for presentation to the user. Each exercise can require use of an exercise apparatus. The exercise can be mapped to at least one exercise apparatus located at the fitness facility. A target exercise apparatus can be identified from the mapped exercise apparatus(es). Location information for one or more of the target exercise apparatuses can be provided for presentation to the user. As used herein, unless otherwise noted, the term "set" means one or more (i.e., at least one) and the phrase "any solution" means any now known or later developed solution.

Turning to the drawings, FIG. 1 shows an illustrative environment 10 for managing access to exercise equipment in a fitness facility according to an embodiment. To this extent, environment 10 includes a computer system 20 that can perform a process described herein in order to manage access to exercise apparatuses 14 in a fitness facility. In particular, computer system 20 is shown including a management program 30, which makes computer system 20 operable to manage access to exercise apparatuses 14 in a fitness facility by performing a process described herein.

Computer system 20 is shown including a processing component 22 (e.g., one or more processors), a storage component 24 (e.g., a storage hierarchy), an input/output (I/O) component 26 (e.g., one or more I/O interfaces and/or devices), and a communications pathway 28. In general, processing component 22 executes program code, such as management program 30, which is at least partially fixed in storage component 24. While executing program code, processing component 22 can process data, which can result in reading and/or writing transformed data from/to storage component 24 and/or I/O component 26 for further processing. Pathway 28 provides a communications link between each of the components in computer system 20. I/O component 26 can comprise one or more human I/O devices, which enable a human user 12 to interact with computer system 20 and/or one or more communications devices to enable a system user 12 to communicate with computer system 20 using any type of communications link. To this extent, management program 30 can manage a set of interfaces (e.g., graphical user interface(s), application program interface, and/or the like) that enable human and/or system users 12 to interact with management program 30. Further, management program 30 can manage (e.g., store, retrieve, create, manipulate, organize, present, etc.) the data, such as management data 40, using any solution.

In any event, computer system 20 can comprise one or more general purpose computing articles of manufacture (e.g., computing devices) capable of executing program code, such as management program 30, installed thereon. As used herein, it is understood that "program code" means any collection of instructions, in any language, code or notation, that cause a computing device having an information processing capability to perform a particular action either directly or after any combination of the following: (a) conversion to another language, code or notation; (b) reproduction in a different material form; and/or (c) decompression. To this extent, management program 30 can be embodied as any combination of system software and/or application software.

Furthermore, management program 30 can be implemented using a set of modules 32. In this case, a module 32 can enable computer system 20 to perform a set of tasks used by management program 30, and can be separately developed and/or implemented apart from other portions of management program 30. As used herein, the term "component" means any configuration of hardware, with or without software, which implements the functionality described in conjunction therewith using any solution, while the term "module" means program code that enables a computer system 20 to implement the actions described in conjunction therewith using any solution. When fixed in a storage component 24 of a computer system 20 that includes a processing component 22, a module is a substantial portion of a component that implements the actions. Regardless, it is understood that two or more components, modules, and/or systems may share some/all of their respective hardware and/or software. Additionally, it is understood that some of the functionality discussed herein may not be implemented or additional functionality may be included as part of computer system 20.

When computer system 20 comprises multiple computing devices, each computing device can have only a portion of management program 30 fixed thereon (e.g., one or more modules 32). However, it is understood that computer system 20 and management program 30 are only representative of various possible equivalent computer systems that may perform a process described herein. To this extent, in other embodiments, the functionality provided by computer system 20 and management program 30 can be at least partially implemented by one or more computing devices that include any combination of general and/or specific purpose hardware with or without program code. In each embodiment, the hardware and program code, if included, can be created using standard engineering and programming techniques, respectively.

Regardless, when computer system 20 includes multiple computing devices, the computing devices can communicate over any type of communications link. Further, while performing a process described herein, computer system 20 can communicate with one or more other computer systems using any type of communications link. In either case, the communications link can comprise any combination of various types of optical fiber, wired, and/or wireless links; comprise any combination of one or more types of networks; and/or utilize any combination of various types of transmission techniques and protocols.

As discussed herein, management program 30 enables computer system 20 to manage access to exercise equipment in a fitness facility. To this extent, management program 30 can utilize management data 40 corresponding to each of a plurality of exercise apparatuses 14 located within the fitness facility to provide access information for use by one or more users 12. As used herein, the term "exercise apparatus" 14 means any equipment, structure, machine, hardware, and/or the like, which a user 12 can utilize in order to perform a desired exercise. To this extent, exercise apparatuses 14 can be utilized for weight-related exercises, cardio-related exercises, and/or the like, and can be configured to target one or more muscle areas and/or bodily systems. Illustrative exercise apparatuses 14 include, but are not limited to, an exercise machine (e.g., elliptical, treadmill, exercise bike, stepper, rower, etc.), a single-use exercise structure (e.g., press/curl machines, etc.), a multi-use exercise structure (e.g., a power system/rack, multi stack gym, etc.), and/or the like. Furthermore, an exercise apparatus 14 can include one or more accessories, each of which also can comprise an exercise apparatus 14. An accessory can be currently attached to a corresponding exercise apparatus 14, or can be located somewhere within the fitness facility, which may or may not be near the exercise apparatus. Additionally, an exercise apparatus 14 can include a designated area/structure, which can be concurrently utilized by more than one individual, such as a track, a swimming pool, a class area (e.g., for Pilates, aerobics, yoga, etc.), a court (e.g., basketball, tennis, squash, racquetball, etc.), and/or the like.

In an embodiment, computer system 20 manages management data 40 corresponding to each of a plurality of exercise apparatuses 14 located within the fitness facility. The management data 40 can include, for example, data corresponding to a location of the exercise apparatus 14 within the fitness facility, data corresponding to a set of exercises for which the exercise apparatus 14 can be utilized, data corresponding to an operating status of the exercise apparatus 14, and/or the like. Additionally, the management data 40 can include dynamically updated data regarding the exercise apparatus 14, such as an indication as to whether the exercise apparatus 14 is currently being utilized, an indication as to whether additional individuals can use the exercise apparatus 14, an indication from a user 12 that an exercise apparatus 14 is inoperable/malfunctioning, and/or the like.

Similarly, computer system 20 can manage management data 40 corresponding to each of a plurality of exercises capable of being performed at a fitness facility. For example, computer system 20 can include management data 40 identifying an exercise name and a corresponding set of exercise apparatuses 14, which are located at the fitness facility and are capable of being used to perform the exercise. It is understood that an exercise may require the concurrent use of multiple exercise apparatuses (e.g., an exercise machine and one or more accessories operable with the machine). In this case, an exercise apparatus 14 in the set of exercise apparatuses 14 can comprise a compound exercise apparatus 14. The compound exercise apparatus 14 can define a primary exercise apparatus 14 (e.g., the exercise machine, which is generally not movable by a user 12) and a set of accessory exercise apparatuses 14 (e.g., the accessory(ies) required for performing the exercise using the exercise machine, which may be located anywhere within the fitness facility).

Additionally, computer system 20 can manage management data 40 corresponding to a set of exercise routines. Each exercise routine can include data corresponding to one or more exercises that can be performed during a single visit to the fitness facility. The exercise routine can comprise any of various amounts of detail and/or any of various types of formatting. For example, for an exercise included in the exercise routine, the exercise routine can include data corresponding to: an exercise name, a planned amount of the exercise (e.g., repetitions, weights, distance, time, and/or the like), and/or the like. Furthermore, the exercise routine can specify a desired order in which one or more of the exercises in the exercise routine are to be performed. However, it is understood that an exercise routine can include more or less data.

Even further, computer system 20 can manage management data 40 corresponding to a set of exercise regimens. Each exercise regimen can include data corresponding to a plurality of exercise routines, which are to be performed in a specified order and/or over a specified time period. For example, an exercise regimen can include data indicating a plurality of exercise routines are to be performed in a particular sequence, which is then repeated as long as the individual wants to participate in the exercise regimen. Alternatively, an exercise regimen could define a series of exercise routines, which are intended to bring the individual to a desired fitness-related goal by a particular date. In an embodiment, computer system 20 includes a plurality of predefined exercise routines and/or predefined exercise regimens, each of which can be obtained from a fitness instructor, a third party fitness program, or the like, and each of which can be configured to provide a workout routine that is intended to provide a particular fitness-related result.

Still further, computer system 20 can manage management data 40 corresponding to a set of members (e.g., user 12). The membership data of each member can include, for example, a membership identification, member contact information, payment information, and/or the like. Furthermore, the membership data can include member historical information, such as a length of time of the membership, a frequency with which the member visits the fitness facility (e.g., determined by a member's checking in to the fitness facility), and/or the like. Still further, as described herein, the membership data can include data corresponding to one or more exercise routines performed by the member, past usage of one or more exercise apparatuses, and/or the like.

Computer system 20 can acquire management data 40 corresponding to each exercise apparatus 14, exercise, exercise routine 42, exercise regimen, and/or member using any solution. For example, some or all of the management data 40 can be manually provided, manually and/or automatically extracted from image data (e.g., video) of the fitness facility, acquired from one or more electronic devices (e.g., sensors, tags (e.g., radio frequency identification (RFID) tags), etc.) associated with the exercise apparatus 14 and/or member, acquired from a third party system (e.g., location data can be acquired from a global positioning system (GPS) provider), and/or the like. Regardless, computer system 20 can store the management data 40 using any combination of various types of data stores, such as a database, an electronic data file, and/or the like.

In any event, computer system 20 can use management data 40 to manage access to the various exercise apparatuses 14 in a fitness facility. As part of managing access to the exercise apparatuses 14, computer system 20 can provide location information for an exercise apparatus 14, which is available for use by a user 12. To this extent, FIG. 2 shows an illustrative method for providing location information for an exercise routine for presentation to a user 12, which can be implemented by computer system 20, according to an embodiment. In particular, computer system 20 uses a planned exercise routine 42 and management data 40 to assist the user 12 in accessing the exercise apparatuses 14 available in the fitness facility in order to perform the exercise routine 42.

Referring to FIGS. 1 and 2, in process 202, computer system 20 receives data corresponding to a planned exercise routine 42 for a user 12. The data can include, for example, data corresponding to a name (e.g., provided by the user 12) of the exercise routine 42, one or more particulars with respect to an exercise (e.g., repetitions, weights, distance, time, and/or the like), a planned order for performing a plurality of exercises, a planned arrival time/date, data identifying a membership of the user 12, and/or the like. Once defined by the user 12, computer system 20 can store data corresponding to a planned exercise routine 42 as a customized exercise routine 42 for the user 12 in the management data 40 (e.g., as membership data for the user 12). Similarly, computer system 20 can store data corresponding to a customized exercise regimen, which includes multiple exercise routines 42 as a customized exercise regimen for the user 12 in the management data 40.

Computer system 20 can obtain the data corresponding to the planned exercise routine 42 using any solution. In an embodiment, computer system 20 manages an interface, such as a graphical user interface, which enables the user 12 to enter his/her planned exercise routine 42 using any solution. For example, user 12 can: manually enter data corresponding to an exercise in the exercise routine 42 into a set of data fields; select a set of exercises from a plurality of exercises defined in the management data 40; select a predefined/customized exercise routine and/or exercise regimen from the management data 40; and/or the like. Furthermore, computer system 20 can automatically or semi-automatically determine the exercise routine 42 for the user 12, e.g., when the user 12 only follows a single exercise routine 42, based on a next scheduled exercise routine as part of an exercise regimen for the user 12, and/or the like. In an embodiment, the interface can be provided for use by the user 12 over a public data network, such as the Internet. In another embodiment, computer system 20 can import the data corresponding to the planned exercise routine 42, e.g., from data entered by the user 12 in a free form, from data managed by an external system (e.g., another fitness facility, a fitness instructor, and/or the like) using any solution. Regardless, the user 12 can access and define the planned exercise routine 42 using any type of device, such as a smart device, a personal computing device, a terminal, and/or the like.

In process 204, computer system 20 can map each exercise defined in the planned exercise routine 42 to a set of exercise apparatuses 14 in the fitness facility. For example, using management data 40, computer system 20 can identify, for each exercise in the planned exercise routine 42, a set of exercise apparatuses 14 located at the fitness facility that can be utilized by the user 12 in performing the exercise. However, an exercise can be referred to using multiple, synonymous names. Additionally, an exercise can have one or more comparable exercises, each of which can be performed using a distinct, but comparable exercise apparatus 14.

To this extent, FIG. 3 shows an illustrative method for mapping exercises in the planned exercise routine 42 to exercise apparatuses in a fitness facility, which can be implemented by computer system 20, according to an embodiment. Referring to FIGS. 1 and 3, in process 302, computer system 20 can get the next (e.g., first) exercise in the planned exercise routine 42 (FIG. 2) using any solution. For example, the planned exercise routine 42 can include an explicitly defined order for the exercises, which computer system 20 can use to identify the next exercise. Alternatively, computer system 20 can infer an order of the exercises, e.g., based on the order in which they appear in the planned exercise routine 42.

In process 304, computer system 20 can map the exercise to a set of generic exercises. In an embodiment, each generic exercise is comparable or identical to the exercise included in the planned exercise routine 42 and can be performed by an individual using a corresponding exercise apparatus that is located at the fitness facility. Computer system 20 can perform the mapping using any solution. For example, management data 40 can include data identifying one or more of the exercises identified in the management data 40 as being comparable to one another. Computer system 20 can use such data to generate the set of generic exercises from the exercise included in the planned exercise routine 42.

Additionally, computer system 20 can use data identifying synonymous exercise names for the various exercises included in the management data 40. For example, computer system 20 can manage and/or access a data store that includes mappings of the exercise names to one another. Such mappings can indicate whether the corresponding exercises are identical (e.g., two names for the same exercise), comparable (e.g., different exercises that have the same intended fitness-related result, and/or the like. Computer system 20 can use such mappings to sort the set of generic exercises according to which one is likely to be most desired by the user 12. Additionally, when computer system 20 fails to map an exercise in the planned exercise routine 42 to any exercises available at the fitness facility, computer system 20 can enable the user 12 to make a correction to the identified exercise, manually identify the exercise from a list of available exercises, remove the exercise from the planned exercise routine 42, and/or the like.

In process 306, computer system 20 can determine whether the exercise was successfully mapped into a set of generic exercises. If not, in process 307, computer system 20 can exit from the process and return information corresponding to the failed mapping. For example, computer system 20 can identify the exercise(s) included in the planned exercise routine 42, which could not be mapped to any of the exercises available at the fitness facility. Such a failure could indicate, for example, that the user 12 would not be able to perform all of the desired exercises at the fitness facility.

Otherwise, in process 308, computer system 20 can map the set of generic exercises to a corresponding set of exercise apparatuses 14. Each exercise apparatus 14 in the set of exercise apparatuses 14 can comprise an exercise apparatus 14 located at the fitness facility, which can be used by the user 12 in order to perform one or more of the set of generic exercises. In an embodiment, the set of exercise apparatuses 14 only includes those exercise apparatuses 14 that are currently indicated as being operable at the fitness facility in the management data 40. In this case, any exercise apparatuses 14 that are currently indicated as being inoperable, out for maintenance, and/or the like, will not be included in the set of exercise apparatuses 14. When multiple exercise apparatuses 14 of the same type are located at the fitness facility, the set of exercise apparatuses 14 can include each (e.g., currently operable) exercise apparatus 14 of the particular type. When an exercise requires a compound exercise apparatus 14 (e.g., an exercise machine and one or more accessories), the set of exercise apparatuses 14 can include multiple compound exercise apparatuses 14, each of which is a unique combination of the multiple exercise apparatuses 14. For example, a single accessory required for an exercise may be present in the fitness facility while two exercise machines are present. In this case, the set of exercise apparatuses can include a compound exercise apparatus 14 for each exercise machine combined with the single accessory.

Similar to the set of generic exercises, computer system 20 can rank the set of exercise apparatuses 14 according to a likely preference of the user 12. For example, an exercise apparatus for the named exercise is likely more preferable than exercise apparatus for an exercise that is comparable to the named exercise. Similarly, an exercise apparatus 14 that is capable of performing multiple exercises in an exercise routine can be more preferable than an exercise apparatus 14 capable of performing fewer. Still further, a compound exercise apparatus 14 having all of the corresponding exercise apparatuses 14 located relatively close to one another (e.g., the accessories are close to or installed on the primary machine) can be more preferable than a compound exercise apparatus in which one or more of the corresponding exercise apparatuses are located farther away. Additionally, in the event that a set of generic exercises cannot be mapped to any exercise apparatuses 14 (e.g., since no appropriate exercise apparatuses are currently operable), computer system 20 can enable the user 12 to remove the corresponding exercise from the planned exercise routine 42, manually identify an exercise apparatus 14 from a list of available exercise apparatuses 14, or allow the unavailability to result in a failure of the mapping.

In process 310, computer system 20 can determine whether the set of generic exercises were successfully mapped to a corresponding set of exercise apparatuses 14. If not, in process 311, computer system 20 can exit from the process and return information corresponding to the failed mapping. For example, computer system 20 can identify the exercise(s) included in the planned exercise routine 42, which could not be mapped to any of the exercise apparatuses 14 currently operable at the fitness facility. Such a failure could indicate, for example, that the user 12 would not be able to perform all of the desired exercises at the fitness facility. Otherwise, in process 312, computer system 20 can determine whether another exercise requires processing in the planned exercise routine 42. If so, the process returns to process 302. Otherwise, in process 314, computer system 20 can return the mappings and exit from the process.

Returning to FIGS. 1 and 2, in process 206, computer system 20 can determine whether all of the exercise(s) were successfully mapped to one or more exercise apparatuses 14 at the fitness facility. If not, in process 207, computer system 20 can provide information regarding the failed mapping for presentation to the user 12. For example, the failure could have been due to an unidentified exercise, no exercise apparatuses 14 present at the fitness facility, no currently operable exercise apparatuses 14 present at the fitness facility, and/or the like.

Otherwise, in process 208, computer system 20 can identify a target exercise apparatus 14 for each exercise in the planned exercise routine 42. In particular, for each exercise in the planned exercise routine 42 including more than one possible exercise apparatus 14, computer system 20 can identify a preferred exercise apparatus from the possible exercise apparatuses 14. In an embodiment, computer system 20 uses location information corresponding to the user 12 and/or the various possible exercise apparatuses 14 to identify the target exercise apparatus 14.

To this extent, FIG. 4 shows an illustrative method for identifying a target exercise apparatus 14 for an exercise, which can be implemented by computer system 20, according to an embodiment. Referring to FIGS. 1 and 4, in process 402, computer system 20 can determine a location of the user 12 and the next exercise in the planned exercise routine 42 (FIG. 2) using any solution. For example, for the first exercise in the planned exercise routine 42, computer system 20 can use an entrance to the fitness facility as the location of the user 12. Subsequently, computer system 20 can use a location of the previously identified target exercise apparatus 14 as the location of the user 12. Similarly, as discussed herein, computer system 20 can use information in the planned exercise routine 42 to identify and/or infer a first exercise in the planned exercise routine 42.

In process 404, computer system 20 can identify the target exercise apparatus 14 for the current exercise from the set of mapped exercise apparatuses 14 for the exercise. Computer system 20 can evaluate any combination of various factors to identify the target exercise apparatus 14 when multiple exercise apparatuses 14 are mapped to the current exercise. To this extent, computer system 20 can obtain information 44 on each mapped exercise apparatus from management data 40 (FIG. 1). As described herein, the information 44 can include, for example, a location of an exercise apparatus 14, whether the exercise apparatus 14 is indicated as being currently in use, a use history of the exercise apparatus 14, a current demand for the exercise apparatus 14 and/or a group of identical exercise apparatuses 14, a peak time for demand of the exercise apparatus 14 based on historical data, a versatility of the exercise apparatus 14, relative locations of the exercise apparatuses 14 forming a compound exercise apparatus, and/or the like.

For example, when computer system 20 is identifying a target exercise apparatus 14 for a user 12 currently ready to use the exercise apparatus 14 (e.g., just arriving at the fitness facility), computer system 20 can identify the exercise apparatus 14 located closest to the user 12 and indicated as not being in use as the target exercise apparatus 14. Computer system 20 can evaluate additional factors in identifying the target exercise apparatus 14. For example, when multiple target exercise apparatuses 14 are capable of being utilized for the current exercise, an exercise apparatus 14 that is the least versatile (e.g., capable of being used for the fewest different exercises) or which is in the least demand/has the most apparatuses available can be selected as the target exercise apparatus 14.

Furthermore, computer system 20 can evaluate factors relating to the user's 12 exercise routine. For example, computer system 20 can consider the relative location of the next required exercise apparatus 14 when selecting the current target exercise apparatus 14. Similarly, if a single, multi-use exercise structure can be utilized for multiple consecutive exercises in an exercise routine, computer system 20 can identify such a structure over other comparable exercise apparatuses 14. For a compound exercise apparatus 14, one in which one or more of the accessories are currently installed and/or located nearby can be selected over one that does not have a required accessory nearby. Still further, computer system 20 can evaluate other factors, such as whether the exercise apparatus 14 is suited for a comparable exercise or the exercise provided by the user.

Computer system 20 can use a weighted combination of scores assigned to each of a plurality of mapped exercise apparatuses 14 to automatically identify a target exercise apparatus 14 and/or rank the exercise apparatuses 14 with respect to one another. For example, the weighting can be used to: favor an exercise apparatus 14 for use with a designated exercise over an exercise apparatus 14 for use with an exercise comparable to the designated exercise; favor a currently available exercise apparatus 14 over one being used; favor a closer exercise apparatus 14 over one further away; favor an exercise apparatus 14 that provides the most flexibility for other individuals at the fitness facility (e.g., by selecting a less versatile exercise apparatus 14 that is capable of being used for all of the exercises for the user 12 over a more versatile exercise apparatus 14 that is also capable of being used for other exercises) and/or least inconvenience for the user 12 (e.g., by selecting an exercise apparatus 14 that is capable of being used for all of the exercises for the user 12 over an exercise apparatus 14 that can only be used for some of the exercises); and/or the like. Computer system 20 can assign the weights and scores for each factor being considered using any solution.

In an embodiment, computer system 20 can assist the user 12 in manually selecting the target exercise apparatus 14 from multiple mapped exercise apparatuses 14. For example, computer system 20 can provide information regarding each of the mapped exercise apparatuses 14 for presentation to the user 12, who can select his/her desired exercise apparatus 14. Computer system 20 can include implicit or explicit information identifying a recommended target exercise apparatus 14 from the multiple mapped exercise apparatuses 14 (e.g., according to the weighted combination of scores) using any solution.

In any event, in process 406, computer system 20 can determine whether a target exercise apparatus 14 was successfully identified. If not, in process 407, computer system 20 can return information regarding the failure and exit the process. For example, a target exercise apparatus 14 may not be able to be identified when each mapped exercise apparatus is indicated as being in use or out of service (e.g., broken, down for maintenance, and/or the like). When sufficient information is available (e.g., from the current users of the exercise apparatus(es) 14, usage history of the exercise apparatus(es) 14, anticipated completion of maintenance, and/or the like), computer system 20 can determine when an exercise apparatus 14 is anticipated to be available, and return the information for presentation to the user 12.

Furthermore, in process 406, computer system 20 can enable the user 12 to select to skip and/or remove an exercise for which no exercise apparatus 14 is currently available from his/her exercise routine, in which case computer system 20 can continue processing the remaining of the exercise routine. In process 408, computer system 20 can determine whether the user's 12 exercise routine includes another exercise. If so, processing can return to process 402. Otherwise, in process 401, computer system 20 can return the identified target exercise apparatuses 14 corresponding to the planned exercise routine 42 for the user 12 and exit the process.

Returning to FIGS. 1 and 2, in process 210, computer system 20 can determine whether a target exercise apparatus 14 was successfully identified for the exercises in the planned exercise routine 42. If not, in process 211, computer system 20 can provide information corresponding to the failure for presentation to the user 12 and exit the process. Otherwise, in process 212, computer system 20 can provide location information regarding one or more of the target exercise apparatus (es) 14 for presentation to the user 12. For example, computer system 20 can provide location information for the target exercise apparatus 14 corresponding to the first exercise included in the planned exercise routine 42. The location information can be presented in any manner. For example, computer system 20 can provide graphical and/or text-based directions for use by the user 12 in locating the exercise apparatus 14 from his/her current location. Similarly, computer system 20 can present a map of the fitness facility with the location of the exercise apparatus 14 highlighted. Computer system 20 can provide the location information for multiple exercise apparatuses 14 concurrently and/or in series, e.g., in response to a request from a user 12.

In an embodiment, computer system 20 can reduce an amount of time required by a user 12 to locate all of the desired exercise apparatuses 14 for his/her planned exercise routine 42. For example, when an exercise requires a compound exercise apparatus 14, computer system 20 can provide location information corresponding to a location of an accessory to assist the user 12 in retrieving the accessory and utilizing it in conjunction with the primary exercise machine to perform the exercise. Similarly, when a user 12 enters a fitness facility, such as a new fitness facility, a busy fitness facility, and/or the like, computer system 20 can assist the user 12 in locating an available/appropriate exercise apparatus 14. Such a benefit also can reduce an amount of frustration experienced by the user 12. For example, a fitness company can have multiple fitness facilities, any one of which its members can visit. However, each fitness facility may have different exercise equipment, different configurations of the exercise equipment, and/or the like. By using computer system 20, a user 12 can more readily use the exercise apparatus(es) 14 at an unfamiliar fitness facility.

Computer system 20 also can perform actions that are configured to enhance the user's 12 experience using the fitness facility. For example, computer system 20 can enable a user 12 to indicate that a particular exercise apparatus 14 is inoperable, e.g., by selecting the exercise apparatus from an interface, scanning a barcode, electronic signaling, and/or the like. In response, computer system 20 can provide the user 12 with information regarding an alternative exercise apparatus 14, if available. Furthermore, computer system 20 can flag the exercise apparatus 14 as being potentially inoperable (e.g., after a threshold number of incidents and/or amount of non-use of the exercise apparatus 14), which can be used by computer system 20 to direct other users 12 to alternative exercise apparatuses 14, flag the exercise apparatus 14 for evaluation by a maintenance individual, and/or the like.

Furthermore, computer system 20 can evaluate the user's planned exercise routine 42 and make one or more recommendations for changes to the planned exercise routine 42 based on, for example, management data 40 indicating a set of best practices for exercise routines 42, which can be provided by, for example, a fitness expert. The changes can include, for example, an order in which the exercises are performed, an amount of time, weight, repetitions, and/or the like, for a particular exercise, etc. To this extent, computer system 20 can maintain a history of the exercise routines performed by the user 12 as management data 40, and derive one or more recommendations based on the history.

Additionally, an exercise apparatus 14 can include an interface with computer system 20. For example, one or more settings of the exercise apparatus 14 can be configurable via an electronic interface, which can communicate with computer system 20, e.g., over a network. Furthermore, the exercise apparatus 14 can provide data corresponding to use of the exercise apparatus 14 for processing by computer system 20. In this case, computer system 20 can automatically configure one or more of the exercise apparatuses 14 for use by the user 12, manage a history of the user's 12 exercises, which can be provided for presentation to the user 12 (e.g., via a website), and/or the like. For example, as the user 12 is locating the exercise apparatus 14, computer system 20 can direct the exercise apparatus 14 to configure itself to the amount of weight/resistance, seat position, and/or the like, according to the exercise defined in the exercise routine 42 and/or the user's 12 history/preferences stored in the management data 40.

It is understood that computer system 20 can dynamically determine, update, and/or revise information corresponding to a planned exercise routine 42 and/or the corresponding target exercise apparatus(es) 14 associated therewith. For example, prior to the user 12 requiring use of a target exercise apparatus 14, the exercise apparatus 14 may be flagged as inoperable, may start being used by another user, and/or the like. In response, computer system 20 can automatically or semi-automatically adjust the target exercise apparatus 14 for the user 12 and/or inform the user 12 of the unavailability of the target exercise apparatus 14.

Furthermore, while the illustrative processes shown and described herein are shown processing an entire planned exercise routine 42, it is understood that computer system 20 can process some or all of the planned exercise routine 42 as required. For example, computer system 20 can initially process a planned exercise routine 42 to ensure that the exercises can be completed at a designated fitness facility. Subsequently, the computer system 20 can determine the target exercise apparatus 14 once the user 12 is ready or nearly ready to perform the corresponding exercise. In this manner, the user 12 is not presented with a list of exercise apparatuses 14, which may be unavailable at the time the user 12 desires to perform the exercise. Similarly, when the planned exercise routine 42 includes an anticipated arrival time, computer system 20 can notify the user 12 if no exercise apparatus 14 is anticipated to be available for one or more exercises included in the exercise routine 42 at the arrival time and/or anticipated time that the user 12 desires to perform the exercise. In this case, the user 12 can decide to visit a different fitness facility, adjust the planned exercise routine 42, and/or the like, prior to traveling to the fitness facility.

In an embodiment, computer system 20 can use the planned exercise routine 42 information for a plurality of users 12 to manage access to the exercise apparatuses 14 of a fitness facility. For example, the data corresponding to exercise routines 42 for multiple users 12 may indicate that demand for a particular exercise apparatus 14/type of exercise apparatus 14 exceeds its availability in the fitness facility at a particular time. In this case, computer system 20 can recommend/require adjustments to the exercise routines 42 of some of the users 12 to spread out the demand over time, direct the users 12 to alternative exercise apparatuses 14, and/or the like. Computer system 20 can use any combination of various factors in selecting the user(s) 12 that are required to adjust their planned exercise routines 42. Illustrative factors can include, for example, prior use of the exercise apparatus 14 by each user 12 (e.g., users 12 having used the apparatus less can be given preference over heavy users of the apparatus when other factors are even), a relative seniority of a user 12 with respect to the other users 12, past performance of a comparable exercise using a different exercise apparatus 14 by a user 12, and/or the like.

While shown and described herein as a method and system for managing access to exercise equipment using a planned exercise routine, it is understood that aspects of the invention further provide various alternative embodiments. For example, in one embodiment, the invention provides a computer program fixed in at least one computer-readable medium, which when executed, enables a computer system to manage access to exercise equipment using a planned exercise routine. To this extent, the computer-readable medium includes program code, such as management program 30 (FIG. 1), which implements some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

In another embodiment, the invention provides a method of providing a copy of program code, such as management program 30 (FIG. 1), which implements some or all of a process described herein. In this case, a computer system can process a copy of program code that implements some or all of a process described herein to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of program code that implements some or all of a process described herein, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for managing access to exercise equipment using a planned exercise routine. In this case, a computer system, such as computer system 20 (FIG. 1), can be obtained (e.g., created, maintained, made available, etc.) and one or more components for performing a process described herein can be obtained (e.g., created, purchased, used, modified, etc.) and deployed to the computer system. To this extent, the deployment can comprise one or more of: (1) installing program code on a computing device; (2) adding one or more computing and/or I/O devices to the computer system; (3) incorporating and/or modifying the computer system to enable it to perform a process described herein; and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A computer-implemented method of managing access to exercise equipment in a fitness facility, the method comprising:
   obtaining, via a computer system, electronic data corresponding to an exercise routine for a user, wherein the exercise routine includes an exercise desired to be performed by the user at the fitness facility;
   mapping the exercise to at least one exercise apparatus located at the fitness facility using the computer system;
   identifying a target exercise apparatus at the fitness facility for the exercise from the at least one exercise apparatus located at the fitness facility using the computer system; and
   providing location information for the target exercise apparatus corresponding to the exercise in the exercise routine for presentation to the user.

2. The method of claim 1, wherein the mapping includes:
   mapping the exercise in the exercise routine to an exercise capable of being performed at the fitness facility; and
   mapping the exercise capable of being performed at the fitness facility to at least one exercise apparatus located at the fitness facility.

3. The method of claim 1, wherein the identifying includes selecting the target exercise apparatus based on at least one of: a versatility of each of the at least one exercise apparatus, an operating condition of each of the at least one exercise apparatus, or a location of the at least one exercise apparatus with respect to a previous location of the user.

4. The method of claim 1, further comprising:
   identifying a shortage at the fitness facility for an identified target exercise apparatus for the exercise;
   identifying an alternative exercise apparatus for the exercise; and
   providing location information for the alternative exercise apparatus for presentation to the user.

5. The method of claim 4, wherein the identifying is based on at least one of: a monitored availability of the target exercise apparatus, a reported inoperability of the identified target exercise apparatus, or at least one of: a usage history of the target exercise apparatus by the user and by a second individual desiring to use the identified target exercise apparatus or a relative seniority of the user with respect to the second individual.

6. The method of claim 1, further comprising automatically obtaining current usage data corresponding to a current usage of at least some of a plurality of exercise apparatuses at the fitness facility, wherein the mapping uses the current usage data.

7. The method of claim 1, further comprising providing an alert for presentation to the user in response to failing to identify a target exercise apparatus for the exercise.

8. The method of claim 1, wherein the target exercise apparatus corresponding to the exercise comprises a compound exercise apparatus, the providing location information including providing location information corresponding to an accessory exercise apparatus of the compound exercise apparatus for presentation to the user.

9. A computer system for managing access to exercise equipment in a fitness facility by performing a method, the method comprising:
   obtaining electronic data corresponding to an exercise routine for a user, wherein the exercise routine includes an exercise desired to be performed by the user at the fitness facility;
   mapping the exercise to at least one exercise apparatus located at the fitness facility;
   identifying a target exercise apparatus at the fitness facility for the exercise from the at least one exercise apparatus located at the fitness facility; and
   providing location information for the target exercise apparatus corresponding to the exercise in the exercise routine for presentation to the user.

10. The computer system of claim 9, wherein the mapping includes:
    mapping the exercise in the exercise routine to an exercise capable of being performed at the fitness facility; and
    mapping the exercise capable of being performed at the fitness facility to at least one exercise apparatus located at the fitness facility.

11. The computer system of claim 9, wherein the identifying includes selecting the target exercise apparatus based on at least one of: a versatility of each of the at least one exercise apparatus, an operating condition of each of the at least one exercise apparatus, or a location of the at least one exercise apparatus with respect to a previous location of the user.

12. The computer system of claim 9, the method further comprising:
    identifying a shortage at the fitness facility for an identified target exercise apparatus for the exercise;
    identifying an alternative exercise apparatus for the exercise; and
    providing location information for the alternative exercise apparatus for presentation to the user.

13. The computer system of claim 9, further comprising automatically obtaining current usage data corresponding to a current usage of at least some of a plurality of exercise apparatuses at the fitness facility, wherein the mapping uses the current usage data.

14. The computer system of claim 9, wherein the target exercise apparatus corresponding to the exercise comprises a compound exercise apparatus, the providing location information including providing location information corresponding to an accessory exercise apparatus of the compound exercise apparatus for presentation to the user.

15. A computer program comprising program code embodied in at least one non-transitory computer-readable storage medium, which when executed, enables a computer system to implement a method of managing access to exercise equipment in a fitness facility, the method comprising:
    obtaining electronic data corresponding to an exercise routine for a user, wherein the exercise routine includes an exercise desired to be performed by the user at the fitness facility;
    mapping the exercise to at least one exercise apparatus located at the fitness facility;
    identifying a target exercise apparatus at the fitness facility for the exercise from the at least one exercise apparatus located at the fitness facility; and
    providing location information for the target exercise apparatus corresponding to the exercise in the exercise routine for presentation to the user.

16. The computer program of claim 15, wherein the mapping includes:
    mapping the exercise in the exercise routine to an exercise capable of being performed at the fitness facility; and
    mapping the exercise capable of being performed at the fitness facility to at least one exercise apparatus located at the fitness facility.

17. The computer program of claim 15, wherein the identifying includes selecting the target exercise apparatus based on at least one of: a versatility of each of the at least one exercise apparatus, an operating condition of each of the at least one exercise apparatus, or a location of the at least one exercise apparatus with respect to a previous location of the user.

18. The computer program of claim 15, the method further comprising:
    identifying a shortage at the fitness facility for an identified target exercise apparatus for the exercise;
    identifying an alternative exercise apparatus for the exercise; and
    providing location information for the alternative exercise apparatus for presentation to the user.

19. The computer program of claim 15, further comprising automatically obtaining current usage data corresponding to a current usage of at least some of a plurality of exercise apparatuses at the fitness facility, wherein the mapping uses the current usage data.

20. The computer program of claim 15, wherein the target exercise apparatus corresponding to the exercise comprises a compound exercise apparatus, the providing location information including providing location information corresponding to an accessory exercise apparatus of the compound exercise apparatus for presentation to the user.

* * * * *